(12) United States Patent
Imhof et al.

(10) Patent No.: US 7,790,863 B2
(45) Date of Patent: *Sep. 7, 2010

(54) ANGIOGENESIS INHIBITING MOLECULES AND THEIR USE IN THE TREATMENT AND DIAGNOSIS OF CANCER

(75) Inventors: Beat A. Imhof, Conches (CH); Michel Aurrand-Lions, Geneva (CH)

(73) Assignee: Merck Serono S.A., Coinsins, Vaud (CH)

( * ) Notice: Subject to any disclaimer, the term of this patent is extended or adjusted under 35 U.S.C. 154(b) by 826 days.

This patent is subject to a terminal disclaimer.

(21) Appl. No.: 10/579,105

(22) PCT Filed: Nov. 19, 2004

(86) PCT No.: PCT/EP2004/013247

§ 371 (c)(1),
(2), (4) Date: Feb. 6, 2007

(87) PCT Pub. No.: WO2005/050213

PCT Pub. Date: Jun. 2, 2005

(65) Prior Publication Data

US 2007/0202110 A1    Aug. 30, 2007

Related U.S. Application Data

(63) Continuation-in-part of application No. 10/738,123, filed on Dec. 18, 2003, now Pat. No. 7,642,341.

(30) Foreign Application Priority Data

Nov. 19, 2003   (EP)   .................. 03026629

(51) Int. Cl.
*C07K 16/28* (2006.01)
*A61K 39/395* (2006.01)
*G01N 33/53* (2006.01)
*G01N 33/577* (2006.01)
*C12P 21/08* (2006.01)
*C12N 5/20* (2006.01)

(52) U.S. Cl. .................... 530/388.22; 530/387.3; 424/141.1; 424/155.1; 435/69.1; 435/70.21; 435/328; 435/334; 435/344; 436/512

(58) Field of Classification Search ............. None
See application file for complete search history.

(56) References Cited

U.S. PATENT DOCUMENTS

| | | | |
|---|---|---|---|
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Longberg et al. | |
| 5,712,120 A | 1/1998 | Rodriguez et al. | |
| 5,770,429 A | 6/1998 | Lonberg et al. | |
| 5,789,650 A | 8/1998 | Lonberg et al. | |
| 5,814,318 A | 9/1998 | Lonberg et al. | |
| 5,874,299 A | 2/1999 | Lonberg et al. | |
| 5,877,397 A | 3/1999 | Lonberg et al. | |
| 6,075,181 A * | 6/2000 | Kucherlapati et al. | ......... 800/25 |
| 2003/0017534 A1 | 1/2003 | Buelow et al. | |
| 2004/0208873 A1 | 10/2004 | Teeling et al. | |
| 2005/0136060 A1* | 6/2005 | Imhof et al. | ............. 424/155.1 |
| 2005/0266426 A1 | 12/2005 | Imhof et al. | |

FOREIGN PATENT DOCUMENTS

| | | |
|---|---|---|
| EP | 0843961 | 5/1996 |
| WO | WO 92/03918 | 3/1992 |
| WO | WO 92/22645 | 12/1992 |
| WO | WO 93/01227 | 1/1993 |
| WO | WO 94/25585 | 11/1994 |
| WO | WO 97/07671 | 3/1997 |
| WO | WO 98/24884 | 6/1999 |
| WO | WO 99/45962 | 9/1999 |
| WO | WO 00/53749 | 9/2000 |
| WO | WO 00/53749 A2 | 9/2000 |
| WO | WO 01/14424 | 3/2001 |
| WO | WO 02/43478 | 6/2002 |
| WO | WO 03/006673 A2 | 1/2003 |
| WO | WO 03/0008541 A2 | 1/2003 |
| WO | WO 03/059282 | 7/2003 |
| WO | WO 2004/055056 | 7/2004 |

OTHER PUBLICATIONS

Paul, Fundamental Immunology, 3rd Edition, 1993, pp. 292-295.*
Rudikoff et al (Proc. Natl. Acad. Sci. USA, 79(6):1979-1983, Mar. 1982.*
Colman P. M. (Research in Immunology, 145:33-36, 1994.*
Bendig M. M. (Methods: A Companion to Methods in Enzymology, 1995; 8:83-93.*
MacCallum et al (J. Mol. Biol., 262,732-745, 1996.*
Lederman et al (Molecular Immunology 28:1171-1181, 1991).*
Li et al (Proc. Natl. Acad. Sci. USA 77:3211-3214, 1980).*
Casset et al (Biochemical and Biophysical Research Communications, 307:198-205, 2003).*
Arrate, M.P. et al. "Cloning of human junctional adhesion molecule 3 (JAM3) and its identification as the JAM2 counter-receptor", *The Journal of Biological Chemistry*, Dec. 7, 2001, pp. 45826-45832, vol. 276, No. 49.
Aurrand-Lions, M. et al. "JAM-2, a novel immunoloqlobulin superfamily molecule, expressed by endothelial and lymphatic cells", *Journal of Biological Chemistry*, Jan. 26, 2001, pp. 2733-2741, vol. 276, No. 4.

(Continued)

Primary Examiner—Robert B Mondesi
Assistant Examiner—Padma V Baskar
(74) Attorney, Agent, or Firm—Saliwanchik, Lloyd & Saliwanchik

(57) ABSTRACT

The present invention relates to angiogenesis inhibiting molecules that are the monoclonal antibody H33 or fragments or derivatives thereof, to their use in the treatment of cancer, in particular the treatment of solid tumors and to therapeutic and diagnostic compositions comprising them. The invention relates in particular to humanized derivatives of H33 of human monoclonal antibodies having the specificity of H33.

14 Claims, 7 Drawing Sheets

OTHER PUBLICATIONS

Figure 1:
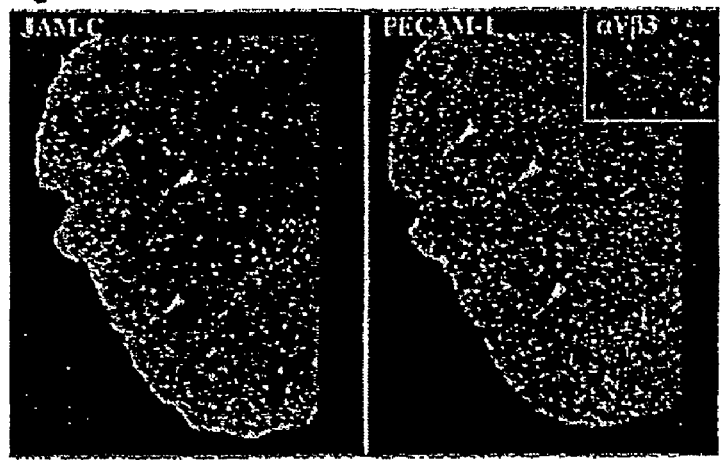

Bazzoni, G. "The JAM family of junctional adhesion molecules", *Current Opinion in Cell Biology*, 2003, pp. 525-530, vol. 15, No. 5.

Johnson-Léger, C. et al. "Junctional adhesion molecule-2 (JAM-2) promotes lymphocyte transendothelial migration", *Blood*, Oct. 1, 2002, pp. 2479-2486, vol. 100, No. 7.

Liang, T. W. et al. "Vascular endothelial-junctional adhesion molecule (VE-JAM)/JAM 2 interacts with T, NK, and dendrittic cells through JAM 3", *Journal of Immunology*, 2002, pp. 1618-1626, vol. 168, No. 4.

Muller, W.A. "Leukocyte—endothelial-cell interactions in leukocyte transmigration and the inflammatory response", *Trends in Immunology*, Jun. 2003, pp. 326-333, vol. 24, No. 6.

Naik, M.U. et al. "Signaling through JAM-1 and $\alpha_v\beta_3$ is required for the angiogenic action of bFGF: dissociation of the JAM-1 and $\alpha_v\beta_3$ complex", *Blood*, Sep. 15, 2003, pp. 2108-2114, vol. 102, No. 6.

Vestweber, D. "Regulation of endothelial cell contacts during leukocyte extravasation", *Current Opinion in Cell Biology*, 2002, pp. 587-593, vol. 14, No. 5.

Vestweber, D. "Molecular mechanisms that control endothelial cell contacts", *Journal of Pathology*, 2000, pp. 281-291, vol. 190, No. 3.

Aurrand-Lions, M. et al. "Heterogeneity of endothelial junctions is reflected by differential expression and specific subcellular localization of the three JAM family members", *Blood*, Dec. 15, 2001, pp. 3699-3707, vol. 98, No. 13.

Chavakis, T. et al. "The junctional adhesion molecule-C promotes neutrophil transendothelial migration in Vitro and in Vivo", *The Journal of Biological Chemistry*, Dec. 31, 2004, pp. 55602-55608, vol. 279, No. 53.

Chen, J. et al. "B cell development in mice that lack one or both immunoglobulin κ light chain genes", *The EMBO Journal*, 1993, pp. 821-830, vol. 12, No. 3.

Chen, J. et al. "Immunoglobulin gene rearrangement in B cell deficient mice generated by targeted deletion of the $J_H$ locus", *International Immunology*, 1993, pp. 647-656, vol. 5, No. 6.

Choi, T.K. et al. "Transgenic mice containing a human heavy chain immunoglobulin gene fragment cloned in a yeast artificial chromosome", *Nature Genetics*, Jun. 1993, pp. 117-123, vol. 4.

Crowther, M. et al. "Microenvironmental influence on macrophage regulation of angiogenesis in wounds and malignant tumors", *Journal of Leukocyte Biology*, Oct. 2001, pp. 478-490, vol. 70.

Cunningham, S.A. et al. "A Novel Protein with Homology to the Junctional Adhesion Molecule", *The Journal of Biological Chemistry*, Nov. 3, 2000, pp. 34750-34756, vol. 275, No. 44.

Fishwild, D.M. et al. "High-avidity human IgGκ monoclonal antibodies from a novel strain of minilocus transgenic mice", *Nature Biotechnology*, Jul. 1996, pp. 845-851, vol. 14.

Harding, F.A. et al. "Class switching in human immunoglobulin transgenic mice", *Annals New York Academy of Sciences*, 1995, pp. 536-546, vol. 764.

Jones, P.T. et al. "Replacing the complementarity-determining regions in a human antibody with those from a mouse", *Nature*, May 29, 1986, pp. 522-525, vol. 321.

Joosten, V. et al. "The production of antibody fragments and antibody fusion proteins by yeasts and filamentous fungi", *Microbial Cell Factories*, 2003, pp. 1-15, vol. 2, No. 1.

Kohler, G. et al. "Continuous cultures of fused cells secreting antibody of predefined specificity", *Nature*, Aug. 7, 1975, pp. 495-497, vol. 256.

Lonberg, N. et al. "Antigen-specific human antibodies from mice comprising four distinct genetic modifications", *Nature*, Apr. 28, 1994, pp. 856-859, vol. 368.

Lonberg, N. et al. "Human antibodies from transgenic mice", *Intern. Rev. Immunol.*, 1995, pp. 65-93, vol. 13.

Lonberg, N. "Transgenic approaches to human monoclonal antibodies", *Handbook of Experimental Pharmacology*, 1994, pp. 49-101, vol. 113.

Merino, R. et al. "The Yaa gene abrogates the major histocompatibility complex association of murine lupus in (NZB × BXSB)$F_1$ Hybrid Mice", *J. Clin. Invest.*, Aug. 1994, pp. 521-525, vol. 94, No.

Morrison, S.L. et al. "Transfectomas provide novel chimeric antibodies", *Science*, Sep. 20, 1985, pp. 1202-1207, vol. 229.

Murdock, C. et al. "Mechanisms regulating the recruitment of macrophages into hypoxic areas of tumors and other ischemic tissues", *Blood*, Oct. 15, 2004, pp. 2224-2234, vol. 104, No. 8.

Padlan, E.A. "A possible procedure for reducing the immunogenicity of antibody variable domains while preserving their ligand-binding properties", *Molecular Immunology*, 1991, pp. 489-498, vol. 28, No. 4/5.

Padlan, E.A. "Anatomy of the antibody molecule", *Molecular Immunology*, 1994, pp. 169-217, vol. 31, No. 3.

Palmeri, D. et al. "Vascular endothelial junction-associated molecule, a novel member of the immunoglobulin superfamily, is localized to intercellular boundaries of Endothelial Cells", *The Journal of Biological Chemistry*, Jun. 23, 2000, pp. 19139-19145, vol. 275, No. 25.

Queen, C. et al. "A humanized antibody that binds to the interleukin 2 receptor", *Proc. Natl. Acad. Sci. USA*, Dec. 1989, pp. 10029-10033, vol. 86.

Riechmann, L. et al. "Reshaping human antibodies for therapy", *Nature*, Mar. 24, 1988, pp. 323-327, vol. 332, No. 24.

Taylor, L.D. et al. "A transgenic mouse that expresses a diversity of human sequence heavy and light chain immunoglobulins", *Nucleic Acids Research*, 1992, pp. 6287-6295, vol. 20, No. 23.

Tuaillon, N. et al. "Human immunoglobulin heavy-chain minilocus recombination in transgenic mice: Gene-segment use in μ and γ transcripts", *Proc. Natl. Acad. Sci. USA*, Apr. 1993, pp. 3720-3724, vol. 90.

Tuaillon, N. et al. "Biased utilization of $D_{HQ52}$ and $J_H4$ gene segments in a human Ig transgenic minilocus is independent of antigenic selection", 1994, pp. 2912-2920, vol. 152.

Verhoeyen, M. et al. "Reshaping human antibodies: grafting an antilysozyme activity", *Science*, Mar. 25, 1988, pp. 1534-1536, vol. 239.

Zen, K. et al. "JAM-C is a component of desmosomes and a ligand for CD11b/CD18-mediated neutrophil transepithelial migration", *Molecular Biology of the Cell*, Aug. 2004, pp. 3926-3937, vol. 15.

Antibody/Collaborator Table, Aug. 14, 2002.

* cited by examiner

ANGIOGENESIS INHIBITING MOLECULES AND THEIR USE IN THE TREATMENT AND DIAGNOSIS OF CANCER

CROSS-REFERENCE TO RELATED APPLICATION

This application is the U.S. national stage application of International Patent Application No. PCT/EP2004/013247, filed Nov. 19, 2004, which is a continuation-in-part of U.S. application Ser. No. 10/738,123, filed Dec. 18, 2003, the disclosures of which are hereby incorporated by reference in their entireties, including all figures, tables and amino acid or nucleic acid sequences.

The present invention relates to molecules that are capable of inhibiting angiogenesis, to therapeutical or diagnostic compositions comprising one or more of the molecules and to the use of such molecules in medicine, in particular in the treatment or diagnosis of cancer, in particular solid tumors. Further disclosed is a method for providing such molecules.

Angiogenesis, the formation of new blood vessels from the pre-existing vasculature is fundamental to wound healing, reproduction and embryonic development. Angiogenesis is also essential for the development of tumors. New blood vessels in tumors provide nutrients allowing the cells to undergo uncontrolled mitosis.

During angiogenesis, endothelial cells proliferate, migrate into new tissue and form inter-endothelial junctions leading to tube formation. This process starts and is driven by angiogenic factors. The signalling of VEGFs and angiopoietins leads to loosening of the pericyte-endothelial contact permitting proliferation and interaction of new endothelial cells with the extracellular matrix mediated by integrins. The $\alpha v \beta 3$ and $\alpha v \beta 5$ integrins have been described to participate in blood vessel development and angiogenesis via a signalling crosstalk with angiogenic factors.

In addition to interactions between endothelial cells and the extra-cellular matrix, the regulation of inter-endothelial contacts is important for tube formation. For example, the adhesion molecule VE-cadherin plays a role in vascular remodelling and maintains integrity of blood vessels.

In the research that led to the present invention the junctional adhesion molecules JAM-B and JAM-C were discovered. These molecules are found in vascular cell-cell contacts and are involved in leukocyte transendothelial migration. Now it was found that the interaction between JAM-B and JAM-C also plays an important role in angiogenesis.

Based on this finding, the inventors tried to find new molecules that are capable of inhibiting angiogenesis. For this they used a method, comprising the steps of:
 a) providing a range of molecules;
 b) testing whether these molecules can prevent interaction between JAM-B and JAM-C;
 c) testing the positive molecules for their ability to block angiogenesis in vivo; and
 d) selecting molecules that are positive in the in vivo test as angiogenesis inhibiting molecules.

Testing the molecules for their ability to block angiogenesis in vivo may be performed by means of the retina test as described in Example 4.

According to the invention it was found that not all molecules that can prevent the interaction between JAM-B and JAM-C are also capable of inhibiting angiogenesis. The additional test of step d) above is therefore necessary to find the desired molecules.

To find molecules that are particularly suitable according to the invention, the method may further comprise the step of testing the positive molecules for their ability to inhibit tumor growth in vivo. The test for inhibiting tumor growth in vivo is for example a test as described in Example 5.

By means of the step of isolating or producing the angiogenesis inhibiting molecules results in the actual obtainment of the desired molecules.

The range of molecules that can be tested in this method can be diverse. The range of molecules can for example suitably be a population of antibodies directed against JAM-B or JAM-C. The preparation of antibodies is a straightforward technique not requiring inventive skill and for example described in Köhler & Milstein, Nature 256:495-497 (1975). The skilled person will therefore be able to provide such range without undue burden.

Testing whether molecules can prevent interaction between JAM-B and JAM-C is for example performed by incubating cells expressing either JAM-B or JAM-C on their surface with labelled soluble JAM-C or JAM-B, respectively, in the presence of said molecules and recording a decrease in labelling of the cells as compared to control incubation without said molecules. Molecules that induce a decrease in the amount of label visualized in comparison to control cells expressing JAM-C or JAM-B and having labelled JAM-B or JAM-C but no molecule to be tested bound to their surface are selected as positive molecules.

Suitable labels are fluorescent, radioactive or Biotin based labels that are well known in the art. Suitable techniques for visualizing the label and disappearance or reduction thereof are flow cytometry, biochemistry, or enzyme linked immunosorbent assay (ELISA).

Molecules that are found to inhibit the interaction between JAM-B and JAM-C are then further tested for their ability to inhibit angiogenesis in vivo. For this various options are available. However, the retina test as described in Example 4 is very well suited because the remodelling of the vasculature depends essentially on endothelial cells and not on microenvironmental factors. Alternative tests are the chorio allantois membrane assay, ischemic reperfusion, or angiogenesis induced by graft of matrigel loaded with angiogenic factors. These tests are well known in the art.

In addition to or instead of testing the ability to inhibit angiogenesis in vivo, the capability of the molecule to inhibit tumor growth in vivo may be tested. A suitable example of such test is as described in Example 5.

The above method finally led to the identification of antibody H33, produced by hybridoma 13H33, deposited on 22 Oct. 2003 with the Deutsche Sammlung von Mikroorganismen und Zellkulturen GmbH under the deposit accession number DSM ACC2622 as an angiogenesis inhibiting molecule of the invention. It was shown that antibody H33, which is directed against JAM-C, can block angiogenesis in vitro and in vivo and prevent tumor growth in vivo. It reduces the recruitment of macrophages into tumors. It can also block the interaction of JAM-C with JAM-B. H33 does not affect proliferation nor apoptosis.

The invention thus relates to the antibody H33 for use as a medicament, in particular for treatment of cancer, more in particular for treating solid tumors. In addition the invention relates to fragments and derivatives of H33, that have the same specificity as H33 for use as a medicament. Such fragments and derivatives are in particular Fab fragments, Fv fragments, single domain antigen binding fragments, recombinant antibodies having the specificity of H33, scFv and aggregates thereof, $V_{HH}$s, humanized derivatives of H33, chimeric antibodies comprising at least the specificity of H33 or human monoclonal antibodies having the specificity of H33.

The latter are suitably produced in transgenic mice or other animals as will be explained hereinbelow.

The invention further relates to antibody fragments and antibody derivatives that retain the antigen binding capacity of the whole antibody as such. Such fragments and derivatives of H33 have not been described in the prior art and are thus novel.

Functional antigen-binding antibody fragments can be engineered by proteolysis of antibodies (papain digestion, pepsin digestions or other enzymatic approaches), yielding Fab, Fv or single domains.

Alternatively, fragments can be produced recombinantly. Fab fragments ("Fragment antigen binding") are the antigen-binding domains of an antibody molecule, containing $V_H + C_H 1$ and $C_L + V_L$. Between $C_L$ and $C_H 1$ an interchain disulfide bond is present. The molecular weight of the heterodimer is usually around 50 kDa. Fab fragments can be prepared by papain digestions of whole antibodies.

The minimal fragment (~30 kDa) that still contains the whole antigen-binding site of a whole IgG antibody is composed of both the variable heavy chain ($V_H$) and variable light chain ($V_L$) domains. This heterodimer, called Fv fragment (for "Fragment variable") is still capable of binding the antigen.

Another fragment is the single domain antigen binding fragment (dAbs) or $V_H$s.

Single-chain Fv fragments can be made recombinantly. In the scFv fragment the $V_H$ and $V_L$ domains are joined with a hydrophilic and flexible peptide linker. scFvs can be complexed into dimers (diabodies), trimers (triabodies) or larger aggregates the monomeric units of which can have the same or different specificities.

A further type of antibody fragment are the $V_{HH}$s comprising the smallest available intact antigen-binding fragment. $V_{HH}$s can be produced from proteolysed heavy chain antibodies of an immunised camelid or via recombinant techniques.

When using recombinant DNA techniques, basically, a polynucleotide encoding the V domain of the H chain or of the L chain of the H33 antibody may be fused with a polynucleotide coding for the constant region of a preferably human H or L chain. For the purpose of expressing the complete H and L chains obtained in this way, a sequence coding a signal peptide allowing the secretion of the protein can also be added.

For producing the angiogenesis inhibiting molecules of the invention, expression cassettes are used, wherein a fused polynucleotide of the invention is linked to appropriate control sequences allowing the regulation of its transcription and translation in a chosen host cell, and recombinant vectors comprising a polynucleotide or such an expression cassette.

Polynucleotides of the invention, i.e. angiogenesis inhibiting molecules that have the specificity of H33, can thus easily be obtained by the well-known methods of recombinant DNA technology, but also by chemical DNA synthesis.

Recombinant DNA constructs can be obtained and introduced in host cells by the well-known techniques of recombinant DNA and genetic engineering.

Useful host cells within the framework of the present invention can be prokaryotic or eukaryotic cells. Among suitable eukaryotic cells, one will mention, by way of example, plant cells, cells of yeasts such as *Saccharomyces*, cells of insects such as *Drosophila*, or *Spodoptera*, and mammal cells such as HeLa, CHO, 3T3, C127, BHK, COS, etc.

There are several methods for transfecting prokaryotic or eukaryotic cells with vectors containing the nucleic acid constructs encoding the chimeric Ig chain. A preferred way of introducing a vector into lymphoid cells is by spheroblast fusion. (see, e. g., Gillies et al. (1989) Biotechnol. 7: 798-804). Alternative methods include electroporation or calcium phosphate precipitation. Other useful methods of producing the immunoconjugates include the preparation of an RNA sequence encoding the construct and its translation in an appropriate in vivo or in vitro system.

Once expressed, the proteins of the invention can be harvested by standard protein purification procedures (see, e. g., U.S. Pat. No. 5,650,150).

When heavy and light chains are combined in the molecule of the invention, the heavy chain of an antibody variable region is preferably co-expressed in the same cell with a corresponding light chain. For fusion proteins that comprise multiple polypeptide chains, more than one expression vector can be used. Co-transfection methods using, for example, two expression vectors, frequently result in both vectors being delivered to a target cell. Alternatively, it is sometimes useful to use a single vector encoding a plurality of polypeptides for co-expression in the same cell.

Furthermore, it can be convenient to express the protein of the present invention as single-chain molecule. For example, an antibody variable region can be expressed as a single chain antibody or sFv optionally fused to a non-immunoglobulin protein. In another embodiment, a heavy chain (with or without a fused cytokine) is combined with a light (or heavy) chain counterpart (with or without a fused cytokine) to form monovalent and divalent immunoconjugates.

The VL and VH regions can be linked by a disulfide bond or a peptide bond, depending on how their nucleic acid sequences are constructed. In general, V regions are linked by a disulfide bond when their sequences are encoded on separate DNA constructs. In contrast, the V regions are typically linked by a peptide bond when their sequences are encoded on a single-chain DNA construct.

In certain embodiments of the invention, the light chain variable region and the heavy chain variable region can be coupled, respectively, to a light chain constant region and a heavy chain constant region of an immunoglobulin. Either kappa or lambda chains of the immunoglobulin light chains constant regions can be used.

The construction of expression vectors of the invention, and the transformation of host-cells can be made by the standard techniques of molecular biology.

The angiogenesis inhibiting molecules of the invention produced by such prokaryotic or eukaryotic cells can be purified from the cells or culture supernatants by affinity chromatography using protein A Sepharose and assessed for their JAM-C binding activity by measuring their inhibitory activities against the binding of H33 to soluble JAM-C coated on microtiter plates by means of well known competitive ELISA technologies.

The remaining rat variable domains may still be immunogenic in humans, and can thus impair the efficacy of an antibody-based therapy. Well known approaches to reduce immunogenicity can be applied, such as "veneering" and "humanization", which involve the introduction of amino acid substitutions as described in patent WO2004055056. Subsequent screening for binding affinity can be performed as described above by mean of inhibitory activity against H33.

Alternatively, non-human T cell epitopes are mutated so that they correspond to human self epitopes that are present in human antibodies (see, for example, U.S. Pat. No. 5,712,120). H33 antibodies are part of the invention having VL and VH regions that include at least one humanized sequence, thereby reducing immunogenicity when administered to a human.

Subsequent antibody production in host cell and purification can be performed as described above.

According to another aspect of the invention, the antibody variable region of H33 or a similar molecule can be linked, with or without an intervening Fc portion, to a non-immunoglobulin moiety. Specifically, the non-immunoglobulin moiety can be a cytokine, such as an interleukin, a hematopoietic factor, a lymphokine, an interferon, or a chemokine. The interleukin can be, for example, interleukin-2 or interleukin-12. The hematopoietic factor and lymphokine can be, for example, granulocyte-macrophage colony stimulating factor (GM-CSF) and a lymphotoxin, respectively. The interferon can be, for example, interferon-α, interferon-β, or interferon-γ.

In some embodiments of the invention, the fusion protein includes a second non-immunoglobulin moiety, such as a second cytokine.

The invention also provides the use of the H33 antibody or fragments or derivatives thereof for the preparation of a medicament for preventing JAM-B/JAM-C interaction in a patient.

Such prevention may comprise targeting a cell with JAM-C on its surface by administering an antibody with variable regions of the present invention to a patient. In one embodiment, the targeted cell is a tumor cell.

According to further aspects of the invention the prevention of JAM-C/JAM-B interaction can be effected by using a nucleic acid encoding the antibody variable region or a cell that includes this nucleic acid, either of which can that is administered to a patient.

For clinical use in humans, it may be helpful to modify the rat-derived antibody H33 to reduce or minimize the immunogenicity of the antibody. As a means of reducing immunogenicity of murine antibodies, various methods have been reported in the literature. Such methods include the production of chimeric antibodies which contain murine or rat variable regions and human constant regions, the production of single chain antibodies which comprise variable binding sequences derived from murine or rat antibodies, the production of antigen-binding fragments of murine or rat antibodies which because of their smaller size are potentially less immunogenic, the production of human monoclonal antibodies and the production of "humanized" antibodies.

Humanization ideally provides an antibody that is non-immunogenic, with complete retention of the antigen-binding properties of the parent non-human antibody molecule. Non-immunogenicity allows for the administration of multiple dosages without adverse immunogenic reaction. Various methods for producing humanized antibodies have been reported in the literature. For example, humanized antibodies can potentially be produced: (a) by grafting only the non-human CDRs onto human framework and constant regions (Jones et al., Nature 321:522-25 (1986); Verhoeyen et al., Science 239:1534-1536 (1988)); or (b) by transplanting the entire non-human variable domains (to preserve ligand-binding properties) but also "cloaking" them with a human-like surface by replacement of exposed residues to reduce immunogenicity (also referred to as "veneered" antibodies) (Padlan, Molec. Immun. 28:489-498 (1991); Padlan, Molec. Immun. 31(3):169-217 (1994)).

Retention of non-human (murine or rat) residues within human variable region framework domains reportedly helps retain proper binding function of the resultant humanized antibody. Humanized antibodies have been reported to potentially decrease or eliminate the immunogenicity of the antibody in a host recipient, thereby permitting an increase in the bioavailability and a reduction in the possibility of adverse immune reactions, thus potentially enabling multiple antibody administrations. Also, the synthesis of the above described scFv and antibody fragments such as Fv, Fd, Fab, Fab', and F(ab)'2 fragments, derived from antibodies having a desired binding specificity comprises another known means of producing targeting moieties having lesser immunogenicity than intact antibodies. Essentially, single chain antibodies and antibody fragments because of their smaller size could be less immunogenic than intact antibodies.

It is also known that recombinant proteins, e.g., antibodies, are glycosylated differently in different host cells used for expression. For the clinical use of H33 antibodies, glycosylation may increase its half-life and/or decrease its immunogenicity.

Antibody H33 can also be used in competition screening to isolate "human monoclonal antibodies" or "recombinant human antibodies" having the same or a similar specificity as H33. Basically, the human antibodies thus isolated can be produced in a hybridoma, transfectoma or in a non-human transgenic animal, e.g., a transgenic mouse, capable of producing multiple isotypes of human monoclonal antibodies to JAM-C (e.g., IgG, IgA and/or IgE) by undergoing V-D-J recombination and isotype switching. (e.g. patents EP1471938 and US2004208873). Such transgenic animal can also be a transgenic rabbit for producing polyclonal antibodies such as disclosed in US 2003/0017534.

The term "human monoclonal antibody" refers to antibodies displaying a single binding specificity which have variable and constant regions derived from human germline immunoglobulin sequences. In one embodiment, the human monoclonal antibodies having the same specificity as H33 are produced by a hybridoma which includes a B cell obtained from a transgenic non-human animal, e.g., a transgenic mouse, having a genome comprising a human heavy chain transgene and a light chain transgene fused to an immortalized cell.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

In a preferred embodiment, human monoclonal antibodies directed against JAM-C and having the specificity of H33 can be generated using transgenic mice carrying parts of the human immune system rather than the mouse system known as "HuMAb" mice. (Lonberg, et al. (1994) Nature 368(6474): 856-859). Accordingly, the mice exhibit reduced expression of mouse IgM or [kappa] light chain, and in response to immunization, the introduced human heavy and light chain transgenes undergo class switching and somatic mutation to generate high affinity human IgG[kappa] monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. Vol. 13:65-93, and Harding, F. and Lonberg, N. (1995) Ann. N.Y Acad. Sci. 764:536-546). The preparation of HuMAb mice is described in detail in Taylor, L. et al. (1992) Nucleic Acids Research 20:6287-6295; Chen, J. et al. (1993) International Immunology 5:647-656; Tuaillon et al. (1993) Proc. Natl. Acad. Sci. USA 90:3720-3724; Choi et al. (1993) Nature Genetics 4:117-123; Chen, J. et al. (1993) EMBO J. 12:821-830; Tuaillon et al. (1994) J. Immunol. 152:2912-2920; Lonberg, N. et al., (1994) Nature 368(6474):856-859; Lonberg, N. (1994) Handbook of Experimental Pharmacology 113:49-101; Taylor, L. et al. (1994) International Immunology 6:579-591; Lonberg, N. and Huszar, D. (1995) Intern. Rev. Immunol. Vol. 13:65-93; Harding, F. and Lonberg, N. (1995) Ann. N.Y Acad. Sci. 764:536-546; Fishwild, D. et al. (1996) Nature Biotechnology 14:845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg, N. and Kay, R. M. and GenPharn International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; and WO 92/03918, published Mar. 19, 1992.

Preferred HuMAb mice have a JKD disruption in their endogenous light chain (kappa) genes (as described in Chen et al. (1993) EMBO J. 12: 821-830), a CMD disruption in their endogenous heavy chain genes (as described in Example 1 of WO 01/14424 by Korman et al.), a KCo5 human kappa light chain transgene (as described in Fishwild et al. (1996) Nature Biotechnology 14:845-851), and a HCo7 human heavy chain transgene (as described in U.S. Pat. No. 5,770,429 by Lonberg, N. and Kay, R. M.) and/or a HCo12 human heavy chain transgene (as described in Example 2 of WO 01/14424 by Korman et al).

Alternatively, mice carrying human immunoglobulin genes on a transchromosomic fragment can be used to generate anti-JAM-C antibodies that have the specificity of H33. Preparation of such trans-chromosomic mice are described in WO97/07671 by Tomizuka et al. A preferred mouse is one in which certain human immunoglobulin genes are carried on a transgene and others are carried on a trans-chromosome, such as a mouse carrying a human light chain transgene (e.g., the KCo5 kappa chain transgene) and a human heavy chain transchromosome (e.g, the SC20 trans-chromosome) as described in detail in WO02/43478 by Ishida et al.

To generate fully human monoclonal antibodies to JAM-C that have the specificity of H33, HuMAb mice can be immunized with a purified or enriched preparation of JAM-C antigen and/or cells producing JAM-C and/or recombinant JAM-C, as described by Lonberg, N. et al. (1994) Nature 368 (6474):856-859; Fishwild, D. et al. (1996) Nature Biotechnology 14:845-851 and WO98/24884. Preferably, the mice will be 6-16 weeks of age upon the first infusion. For example, recombinant JAM-C can be used to immunize the HuMAb mice intraperitoneally.

For producing human monoclonal antibodies to JAM-C, the mouse splenocytes can be isolated and fused with PEG to a mouse myeloma cell line based upon standard protocols. The resulting hybridomas are then screened for the production of antigen-specific antibodies by well known techniques.

Human antibodies of the invention that have the specificity of H33 also can be produced in a host cell transfectoma using, for example, a combination of recombinant DNA techniques and gene transfection methods as is well known in the art (Morrison, S. (1985) Science 229:1202).

H33, fragments or derivatives thereof having the ability to prevent the interaction between JAM-B and JAM-C and to inhibit angiogenesis in vivo can be used in this invention. The production of antibody fragments and antibody fusion proteins is reviewed in Joosten, V. et al., *Microb Cell Fact.* 2(1):1 (2003). Techniques for preparing antibody fragments and derivatives are widely known and can be performed by the person skilled in the field without undue burden.

For example, to express the H33 antibody, or antibody fragments thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used.

The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present).

The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector.

Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc.

Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, non-viral regulatory sequences may be used, such as the ubiquitin promoter or β-globin promoter.

In addition to the antibody chain genes and regulatory sequences, the recombinant expression vectors for expressing angiogenesis inhibiting molecules of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the molecules of the invention in either prokaryotic or eukaryotic host cells, expression in eukaryotic cells, and most preferably mammalian host cells, is the most preferred because such eukaryotic cells, and in particular mammalian cells, are more likely than prokaryotic cells to assemble and secrete a properly folded and immunologically active antibody, fragment or derivative thereof.

Preferred mammalian host cells for expressing the recombinant antibodies of the invention include CHO cells (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NS/0 myeloma cells, COS cells, HEK293 cells and SP2.0 cells. In particular for use with NS/0 myeloma cells, another preferred expression system is the GS (glutamine synthetase) gene expression system disclosed in WO 87/04462, WO 89/01036 and EP 338 841. When recombinant expression vectors encoding antibody genes are introduced into mammalian host cells, the expression products are produced by culturing the host cells for a period of time sufficient to allow for expression of the product in the host cells or, more preferably, secretion of the product into the culture medium in which the host cells are grown. The expression products can be recovered from the culture medium using standard protein purification methods.

Alternatively, the cloned antibody genes can be expressed in other expression systems, including prokaryotic cells, such as microorganisms, e.g., *E. coli* for the production of scFv antibodies, algi, as well as insect cells. Furthermore, the antibodies can be produced in transgenic non-human animals, such as in milk from sheep and rabbits or eggs from hens, or in transgenic plants. See, e.g., Verma, R., et al. (1998). Antibody engineering: Comparison of bacterial, yeast, insect and mammalian expression systems. J. Immunol. Meth. 216:165-181; Pollock, et al. (1999). Transgenic milk as a method for the production of recombinant antibodies. J. Immunol. Meth. 231:147-157; and Fischer, R., et al. (1999). Molecular farming of recombinant antibodies in plants. Biol. Chem. 380: 825-839.

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody, in this case in particular H33, grafted onto framework sequences from a different antibody with different properties (see, e.g., Riechmann, L. et al., 1998, Nature 332:323-327; Jones, P. et al., 1986, Nature 321:522-525; and Queen, C. et al., 1989, Proc. Natl. Acad. See. U.S.A. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody which contains mutations throughout the variable gene but typically clustered in the CDRs. For example, somatic mutations are relatively infrequent in the amino terminal portion of framework region 1 and in the carboxy-terminal portion of framework region 4. Furthermore, many somatic mutations do not significantly alter the binding properties of the antibody.

For this reason, it is not necessary to obtain the entire DNA sequence of a particular antibody in order to recreate an intact recombinant antibody having binding properties similar to those of the original antibody (see WO 99/45962). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion of particular restriction sites, or optimization of particular codons.

In this application, the term "angiogenesis inhibiting molecules" refers to H33 and all possible fragments and derivatives thereof that retain the same or a similar specificity as described herein.

The invention also relates to the use of the angiogenesis inhibiting molecules, such as H33, fragments and derivatives thereof, for the preparation of a therapeutical or diagnostic composition for the treatment or diagnosis of cancer, in particular solid tumors.

The invention also relates to therapeutical or diagnostic compositions for the treatment or diagnosis of cancer, in particular solid tumors, comprising a therapeutically or diagnostically effective amount of one or more angiogenesis inhibiting molecules of the invention and a suitable excipient, carrier, diluent or other additive. The skilled person in the field of cancer therapy will be able to establish the therapeutically or diagnostically effective amount.

The composition may also include a combination of multiple (e.g., two or more) angiogenesis inhibiting molecules of the invention.

Pharmaceutical compositions of the invention can also be administered in combination therapy, i.e., combined with other agents. For example, the combination therapy can include at least one chemotherapeutic agent, at least one anti-inflammatory agent or at least one immunosuppressive agent.

In another embodiment, the angiogenesis inhibiting molecules of the invention may be administered in conjunction with radiotherapy.

In another embodiment, the angiogenesis inhibiting molecules of the invention may be administered in combination with one or more other antibodies, e.g., one or more human antibodies such as, e.g., anti-VEGF antibodies.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The phrases "parenteral administration" and "administered parenterally" as used herein means modes of administration other than enteral and topical administration, usually by injection or infusion, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The angiogenesis inhibiting molecules of the invention may be comprised in the pharmaceutical composition together with a suitable excipient, carrier or diluent.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate.

These compositions may also contain additives such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier.

Regardless of the route of administration selected, the angiogenesis inhibiting molecules of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above.

Administration can suitably be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

For example, when using H33 as the angiogenesis inhibiting molecule, the dosage can be determined or adjusted by measuring the amount of circulating H33 antibodies at different time points following administration in a biological sample by making use of anti-idiotypic antibodies targeting the H33 antibodies or by using other specific methods to detect the H33 antibodies for instance by an ELISA assay using JAM-C as coating.

Therapeutic compositions can also be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the angiogenesis inhibiting molecules of the invention can be formulated to ensure proper distribution in vivo. For example, the blood-brain barrier (BBB) excludes many highly hydrophilic compounds. To ensure that the therapeutic compounds of the invention can cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhancing targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134), different species of which may comprise the formulations of the inventions, as well as components of the invented molecules; p 120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

In one embodiment of the invention, the angiogenesis inhibiting molecules of the invention are formulated in liposomes; in a more preferred embodiment, the liposomes include a targeting moiety. In a most preferred embodiment, the therapeutic compounds in the liposomes are delivered by bolus injection to a site proximal to the desired area, e.g., the site of a tumor. The composition must be fluid to the extent that easy syringability exists. It must be stable under the conditions of manufacture and storage and must be preserved against the contaminating action of microorganisms such as bacteria and fungi.

The efficient dosages and the dosage regimens for the angiogenesis inhibiting molecules of the invention depend on the disease or condition to be treated and can be determined by the persons skilled in the art.

A "therapeutically effective dosage" for tumor therapy can be measured by objective tumor responses which can either be complete or partial. A complete response (CR) is defined as no clinical, radiological or other evidence of disease. A partial response (PR) results from a reduction in aggregate tumor size of greater than 50%. Median time to progression is a measure that characterizes the durability of the objective tumor response.

A "therapeutically effective dosage" for tumor therapy can also be measured by its ability to stabilize the progression of disease. The ability of a compound to inhibit cancer can be evaluated in an animal model system predictive of efficacy in human tumors. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

Accordingly, patients treated with compositions of the invention can be additionally administered (prior to, simultaneously with, or following administration of a molecule of the invention) with another therapeutic agent, which enhances or augments the therapeutic effect of the molecules of the invention.

The invention furthermore also relates to the use of the compounds of the invention in diagnosis. Labeled antibodies can for example be used for locating tumors in the body. Labeling of antibodies with radioactive, paramagnetic or other is a technique well-known in the art.

In a particular embodiment, the invention provides methods for diagnosing diseases associated with JAM-C by detection ex vivo or in vitro of JAM-C in a sample, e.g., a tissue sample, a body fluid sample or a cell sample. This can be achieved, for example, by contacting a sample to be tested, optionally along with a control sample, with the H33 antibody or a derivative or fragment thereof under conditions that allow for formation of a complex between H33 and JAM-C. Complex formation can then be detected (e.g., using an ELISA). When using a control sample along with the test sample, the complex can be detected in both samples and any statistically significant difference in the formation of complexes between the samples is indicative of the presence of JAM-C in the test sample.

The present invention will be further described in the Examples that follow. These Examples are for illustration purposes only and not intended to limit the invention in any way. In the Examples reference is made to the following figures.

FIG. 1 shows that JAM-C is expressed by blood vessels in human liver tumor. JAM-C expression was analysed with a panel of angiogenic tumors. The transcripts encoding human JAM-C are not present in normal liver. Immunostaining of frozen sections with anti-JAM-C antibody shows expression by a subpopulation of blood vessels (arrowheads). Staining with a polyclonal antibody against PECAM-1 to visualize vascular structures is shown on the right panel and the angiogenic characteristic of the tumor was controlled by $\alpha V \beta 3$ staining (insert).

Figure 2:
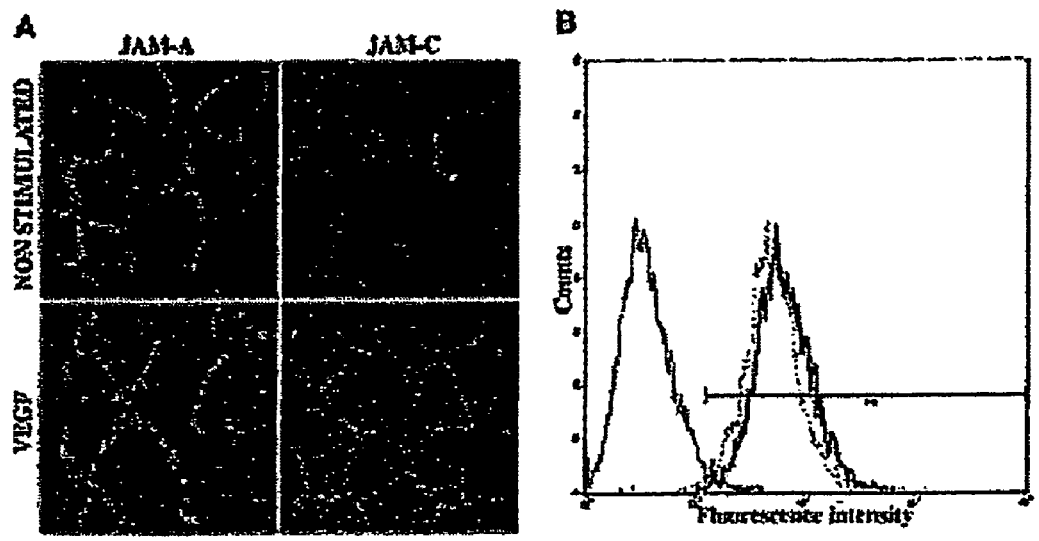

FIG. 2 shows that JAM-C is recruited at inter-endothelial junctions of HUVECs upon VEGF stimulation. (A) HUVECs were stimulated with recombinant VEGF-165, fixed with formaldehyde and JAM-C localization was visualized with anti-JAM-C monoclonal antibody. As control, JAM-A staining was performed. The JAM-C molecule was enriched at cell-cell contacts upon VEGF-165 stimulation whereas no effect was seen with JAM-A. (B) FACS analysis revealed that the enrichment of JAM-C at cell-cell contacts is due to relocalization of the molecule since the expression level remained unchanged after VEGF treatment (thin line, negative control; dashed line, non treated cells; thick line, VEGF treated cells).

Figure 3:
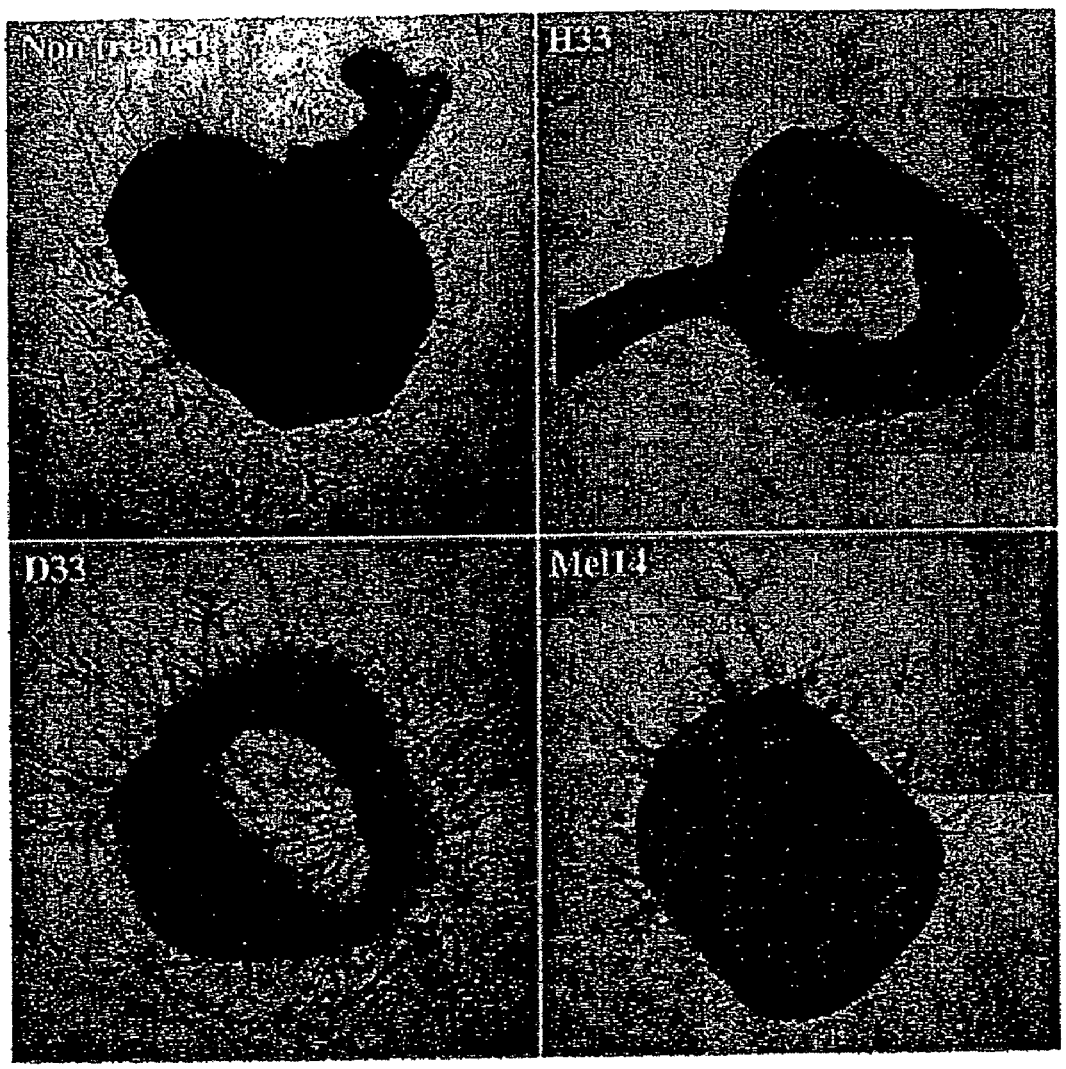

FIG. 3 shows that anti-JAM-C monoclonal antibody abolished angiogenesis in vitro. Aortic rings from mice were grown between two Matrigel layers in the presence or absence of anti-JAM-C antibodies (50 µg/ml) and neovascularization was visualized after 12 days. Pictures are light micrographs of representative non treated (A, n=11) or treated aortic ring microvessels with anti-JAM-C monoclonal antibodies H33 (B, n=11) and D33 (C, n=6) or isotype-matched control antibody Mel14 (D, n=6). Only H33 blocked angiogenic sprouting.

Figure 4:
Figure 4:
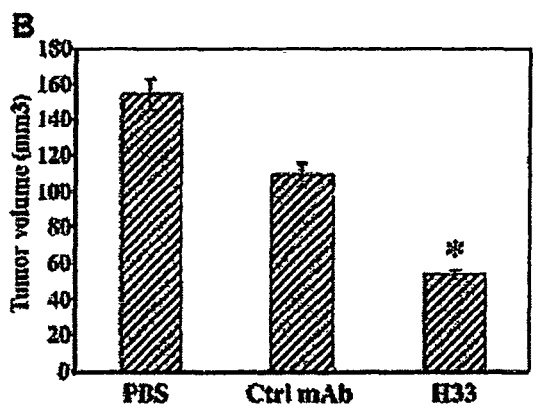
Figure 4:
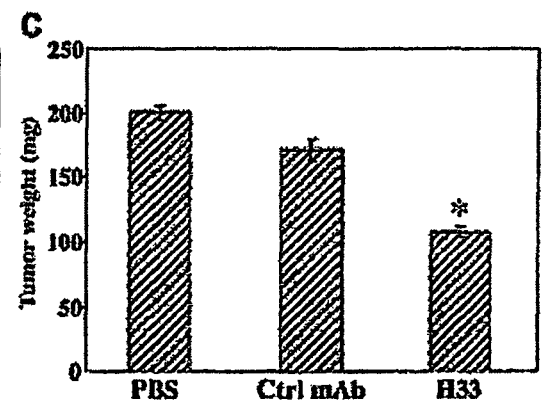
Figure 4:
Figure 4:
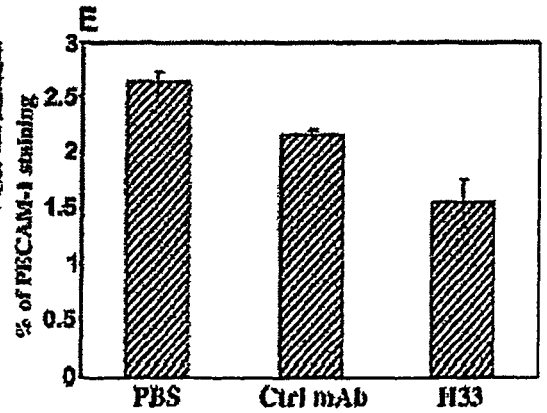

FIG. 4 demonstrates that anti-JAM-C antibody H33 reduced tumor growth and tumor vascularization. Mice were injected sub-cutaneously with LLC1 tumor cells and treated every second day with anti-JAM-C antibody or isotype-matched control antibody (150 µg). (A) macroscopic appearance of 12-day-old LLC1 tumors grown in control mice (PBS and isotype-matched control antibody) or in mice treated with H33 anti-JAM-C antibody. Mice treated with H33 anti-JAM-C antibody show reduced tumor growth as indicated by measurement of tumor volume (B) and tumor weight (C). Microvessels were detected by PECAM-1 immunostaining (D) and quantified by computer analysis (E).* $p<0,01$. Each bar represents the mean value of ten animals tested±sem.

Figure 5:
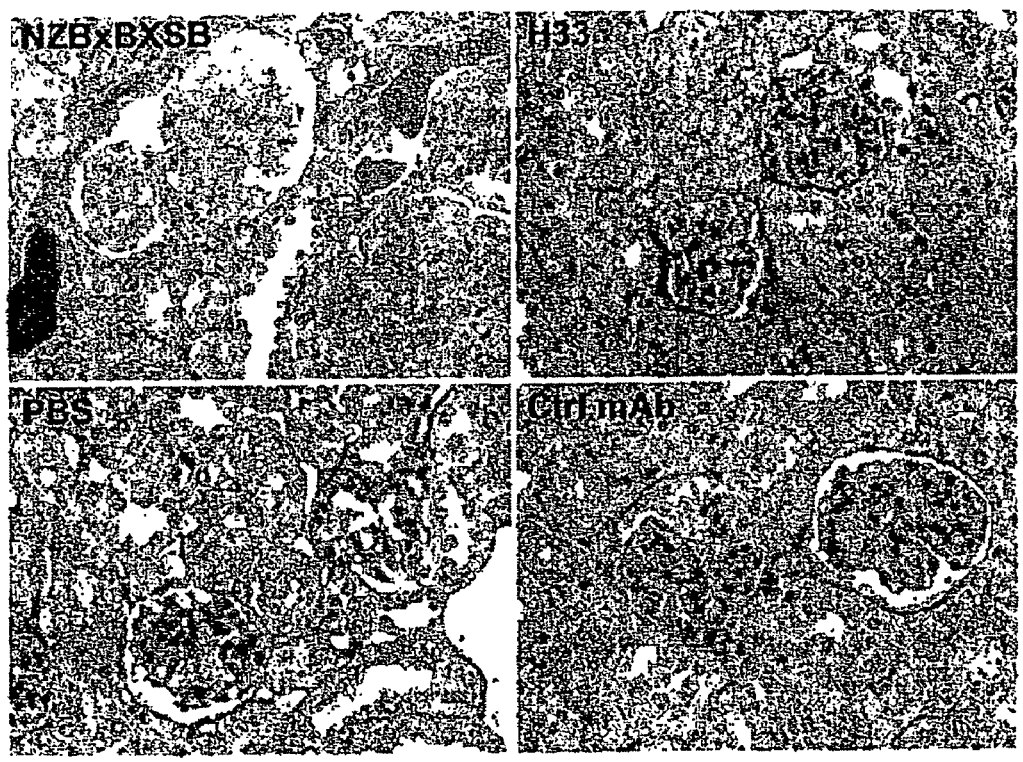
Figure 5:
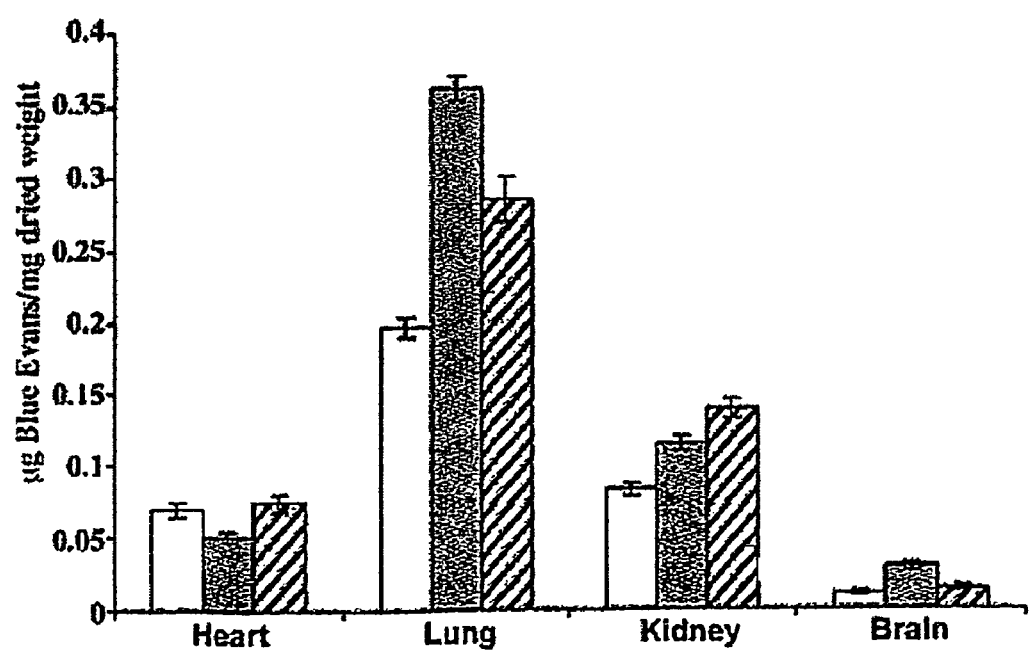

FIG. 5 shows that H33 anti-JAM-C antibody is not toxic in vivo. To ensure that the H33 anti-JAM-C antibody effect on tumor growth was not due to a general toxic effect in vivo, mice were treated as described in FIG. 4 and the organs dissected and analysed. (A) Kidney from these mice stained with periodic acid-Schiff (PAS) did not show any signs of glomerulonephritis development. As control, sections of kidney from autoimmune diseased NZBxBXSB mice were compared (Merino R. et al., *J Clin Invest.* 94(2):521-5 (1994). (B) In vivo blood vessel permeability was assessed using the Evans blue permeability assay. The H33 antibody had no effect on vascular permeability in the representative organs heart, lung, kidney and brain. Each bar represents the mean value of seven animals tested±sem.

Figure 6:
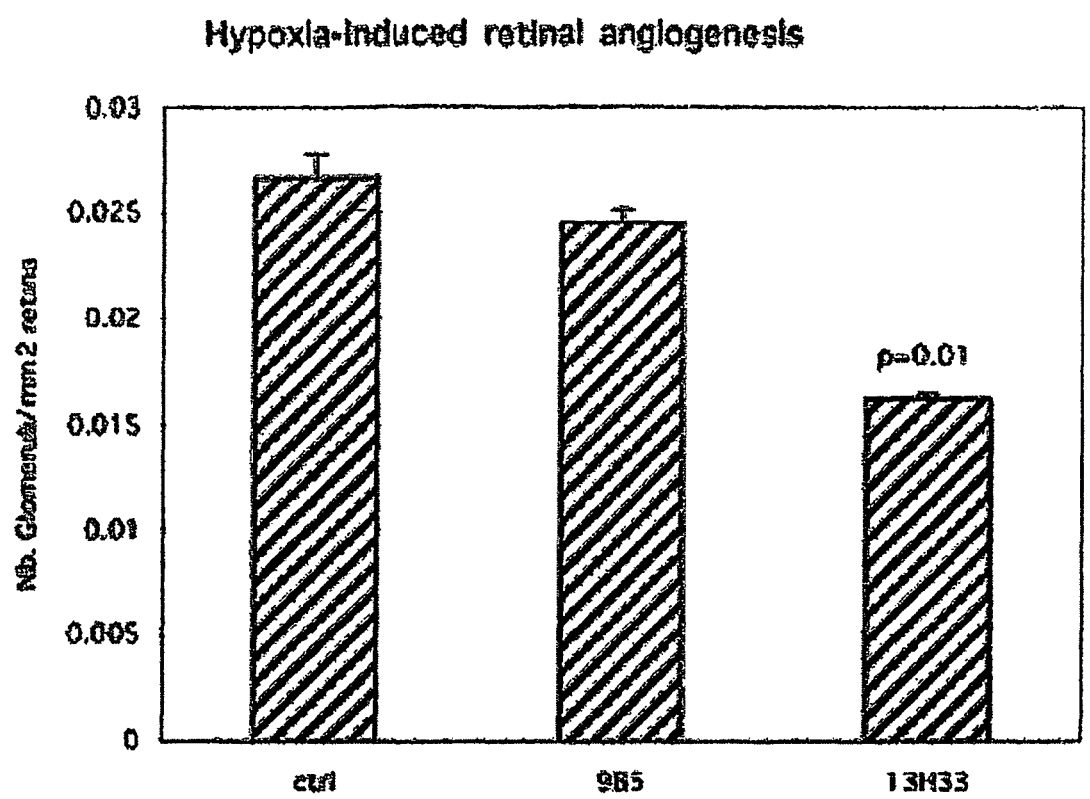

FIG. 6 shows quantitation of glomeruli during revascularization of retinas. The numbers of glomeruli were counted to compare retinal neovascularization in H33-treated and control antibody-treated mice. Reduction in the number of glomeruli was observed in H33 treated (13H33) compared to control mice (ctrl) or mice treated with isotype matched control antibody (9B5). This indicates a decreased neovascularization of retinas in H33 treated animals.

Figure 7:
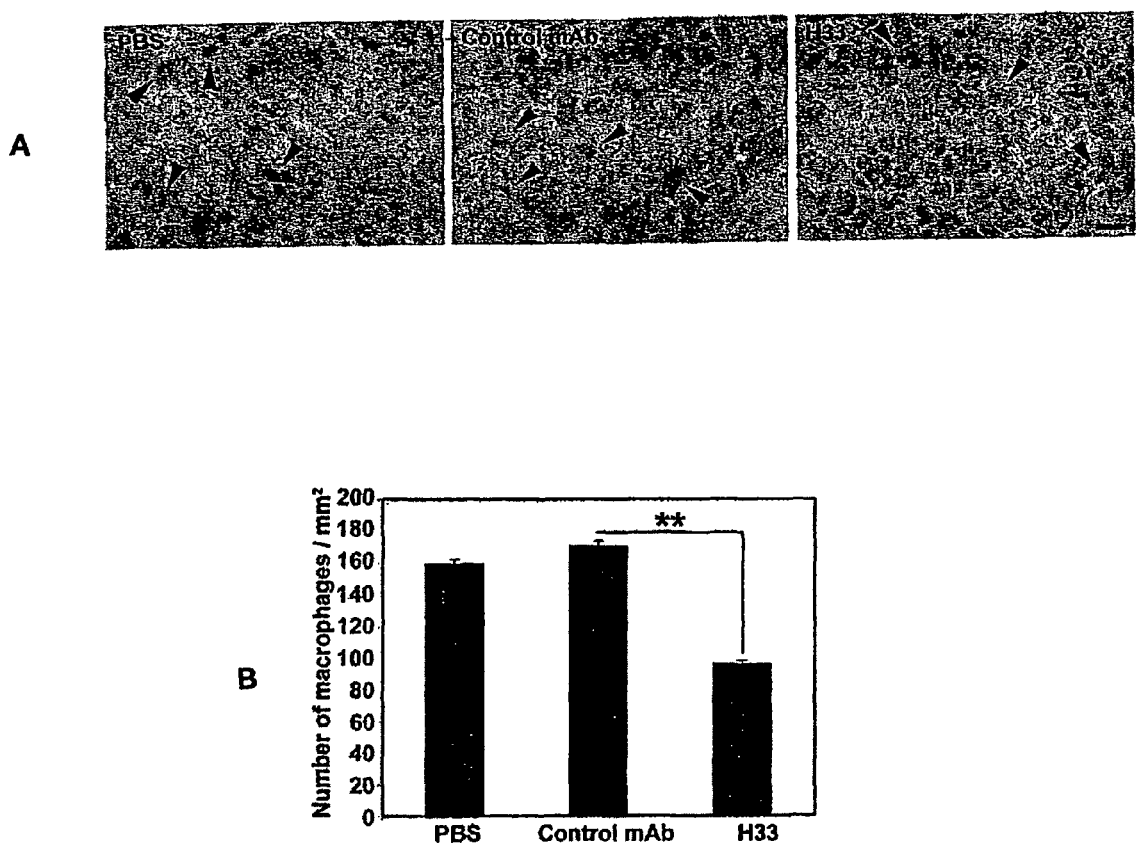

FIG. 7 shows that anti-JAM-C antibody H33 reduces the number of macrophages in tumors. LLC1 tumor cryosections from PBS-, control antibody- or H33-treated mice were stained for acid phosphatase to detect macrophages (A, arrowheads). Microvessel density was quantified by counting the number of labeled macrophages per $mm^2$ within the tumor (B). Tumors from H33-treated animals show reduced infiltrated macrophages, compared to control animals. Each bar represents the mean value±SEM, obtained from four sections of n mice per group (PBS, n=6; control antibody, n=6; H33, n=9). ** p<0.01. Scales bar, (A) 160 mm, (B) 20 mm.

Figure 8:
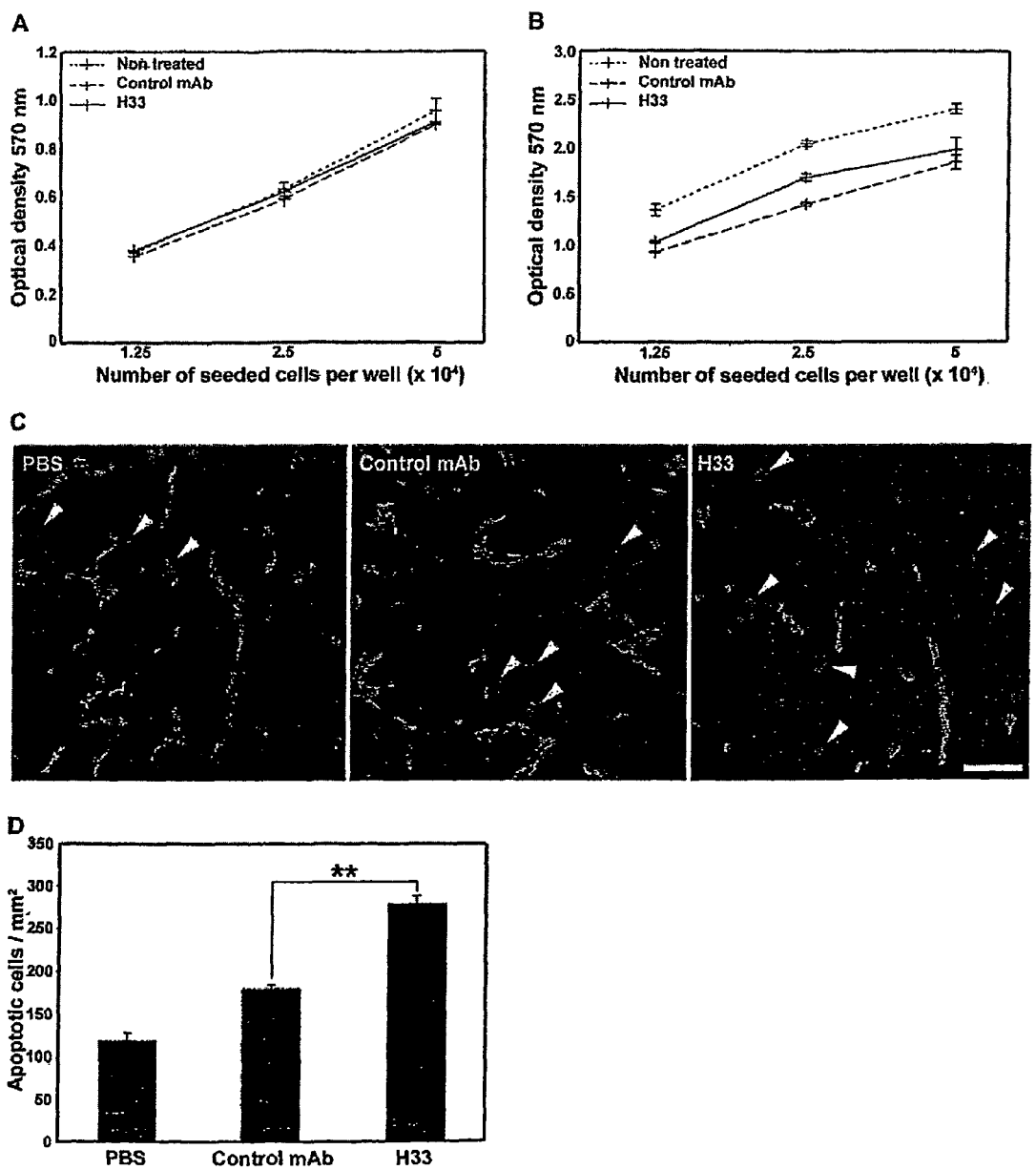

FIG. 8 shows that H33 antibody affects neither proliferation, nor apoptosis of endothelial cells. Endothelial cells (A) or LLC1 tumor cells (B) were seeded ranging from $1.25 \times 10^4$ to $5 \times 10^4$ cells per well and cultured in the presence or absence of either H33 antibody or control antibody. The proliferation rate was determined using MTT assay. H33 antibody does not influence the proliferation of endothelial and tumor cells. (C) LLC1 tumor cryosections from isotype-matched control- or H33-treated mice were immunostained for PECAM-1 (green) and for apoptotic cells with TUNEL staining (red, arrowheads). Endothelial cells do not exhibit an increase in apoptosis when mice were treated with H33 antibody compared to controls. In contrast tumor cells show increased apoptosis as demonstrated by the quantification of apoptotic cells within the tumor (D).

EXAMPLES

Example 1

Preparation of a Population of Antibodies Against JAM-B or JAM-C

A population of antibodies to be tested in the method of the invention is prepared according to Köhler & Milstein, Nature 256:495-497 (1975). The source of antigen to obtain such population of antibodies consist in recombinant soluble JAM-B or JAM-C prepared as described in Example 3.

Example 2

Preparation of Soluble JAM-B and JAM-C

It was found by the present inventors that JAM-C interacts heterophilically with JAM-B through its V domain and that the soluble JAM-C V domain is sufficient for binding to JAM-B.

The soluble JAM-B and the soluble JAM-C V domain were obtained by PCR using the same cloning strategy. Primers were obtained from Microsynth (Microsynth GmbH, Balgach, Switzerland), and restriction sites added for cloning strategy are underlined. The cDNA encoding the extracellular V domain of JAM-C was amplified using plasmid encoding the full length sequence of murine JAM-C, Pfu polymerase, T7 and (5'-gc<u>tctaga</u>cagtgttgccgtcttgcctacag-3') as forward and reverse primers. The PCR product was digested with HindIII and XbaI before cloning in pcDNA3 containing FLAG-tag sequence.

The soluble JAM-B is prepared as follows: The cDNA encoding soluble JAM-B was obtained by PCR using (5'-tcagctaggcagccagct-3') and (5'-gc<u>tctaga</u>atctacttgcattcgcttcc-3') as forward and reverse primers. The PCR product digested with XbaI was then cloned in frame with the FLAG Tag sequence in pcDNA3 using EcoRI/blunt and XbaI sites.

Example 3

Test for the Ability to Prevent Interaction Between JAM-B and JAM-C

Cells expressing either JAM-B or JAM-C on their surface are obtained as described by Aurrand-Lions et al., *J Biol Chem* 276:2733-41 (2001a); Aurrand-Lions et al., *Blood* 98:3699-707 (2001b); Johnson-Leger et al., *Blood* 100:2479-2486 (2002).

Soluble JAM-B and JAM-C obtained as described in Example 2 are labelled with sulfosuccinimidyl esters of Alexa 488 (Molecular Probes Inc.) or sulfo-NHS-Biotin (Pierce) according to the manufacturers procedures.

The cells expressing JAM-B or JAM-C are contacted with the labelled soluble JAM-C or JAM-B, respectively in in the presence of the molecules to be tested. The fluorescence is monitored with flow cytometry and decrease in fluorescence intensity as compared to the non treated control, indicates a decreased binding of soluble JAM-C or soluble JAM-B.

Example 4

Test for the Ability to Block Angiogenesis In Vivo

Postnatal day 7 (P7) mice are placed in 75% oxygen for five days causing central avascularization of retinas (Reynolds et al., *Nature Medicine* 8: 27-34 (2002)). This incubation is followed by housing the mice for five further days (until P17) under normoxic conditions. Mice are injected intraperitoneally with 50 μg of monoclonal antibodies at P12, P14 and P16. Neovascularization is detected by perfusion of the entire vasculature with a non-diffusible fluorescein-dextran solution. In flat-mounted retinas, areas of neovascularization and vascular glomeruli are detected. Vascular glomeruli are highly proliferative clusters of tortuous vessels that are produced in response to angiogenic stimuli and protrude through the inner limiting membrane. The numbers of glomeruli is counted to compare retinal neovascularization in mice treated with a molecule to be tested and in control mice.

One of the molecules tested is monoclonal antibody H33 which caused a reduction in neovascularization.

Example 5

Monoclonal Antibody H33 Directed Against JAM-C is an Inhibitor of Angiogenesis and Tumor Growth 1. Materials and Methods
Antibodies Rat monoclonal antibodies (CRAM) against human and mouse JAM-C (H33, H36 and D33) and rat monoclonal antibodies against mouse PECAM-1/CD31 (GC51) and Lselectin/CD62L (Mel14) were previously described (Aurrand-Lions et al., 2001a, supra; Gallatin et al., *Nature* 330:30-34 (1983); Piali et al., *Eur J Immunol.* 23:2464-71 (1993); Springer et al., *Eur. J. Immunol.* 9:301 (1979). Anti-human CD44 (9B5) used as irrelevant antibody control rat IgG2a was kindly provided by Dr B. Engelhardt (Laschinger and Engelhardt, 2000). Any other unrelated antibody can be used as a negative control. Polyclonal antibody against human JAM-B was prepared according to Palmeri et al., *J Biol Chem.* 275: 19139-45 (2000). Monoclonal mouse anti-human integrin $\alpha v\beta 3$ (LM609) were from Chemicon (Temecula, Calif.).

Endothelial Cells

Human Umbilical Vein Endothelial Cells (HUVEC) were isolated by collagenase treatment of umbilical veins (Wall R T et al., *J Cell Physiol.* 96:203-213 (1978). HUVECs were maintained in M199 supplemented with 20% Fetal Calf Serum (PAA Laboratories), 25 mM HEPES (N-2-hydroxyethylpiperazine-N'-2-ethanesulfonic acid), nonessential amino acids, sodium pyruvate, endothelial cell growth supplement (ECGS, 15 µg/mL; Upstate Biotechnology, Lake Placid, N.Y.), and heparin (4 µg/ml; Sigma, Buchs, Switzerland). Cells were used between passages 3 and 5.

VEGF Stimulation $1.10^5$ HUVECs were plated on Growth Factor Reduced Matrigel (Becton Dickinson, Bedford, Mass., USA). After 48 hours, cells were incubated with 100 ng/ml recombinant human VEGF-165 (PeproTech House, London UK) for 15 minutes (immunocytochemistry) or 15 minutes to 24 hours (Flow cytometry).

Flow Cytometry

HUVECs were incubated with H36 anti-JAM-C monoclonal antibody on ice. After washing with PBS, BSA 0.2% binding of H36 antibody was detected using a phycoerythrin-coupled anti-rat antibody (Jackson Immunoresearch Laboratories, Inc., West Grove, Pa., USA). As control, the primary antibody was omitted. Analysis was performed using FACSCalibur and Cellquest Software (Becton Dickinson, Mountain View, Calif., USA).

Immunostaining

For immunohistochemistry with monoclonal antibody anti-JAM-C (H36) and polyclonal antibody against JAM-B/VE-JAM, frozen sections were fixed with acetone/methanol 1:1 for 5 minutes at −20° C., dried and rehydrated in PBS, Gelatin 0.2%, Tween 20 0.05%. For immunocytochemistry, cells were fixed with paraformaldehyde 4% in PBS for 15 min prior permeabilization with TritonX100 0.01% in PBS for 10 min. Cells were washed with PBS, BSA 0.2%, incubated with primary antibodies for one hour and washed, before further incubation with secondary antibodies coupled to Texas Red, FITC or peroxidase (Jackson Immunoresearch Laboratories, Inc., West Grove, Pa., USA). Pictures were acquired using confocal microscope Zeiss LSM510. Glomerulonephritis was detected by kidney staining with periodic acid-Schiff (PAS).

Ex Vivo Aortic Ring Assay

Mouse aortic ring assays were performed as described (Nicosia, R. F. & Ottinetti, *In Vitro Cell Dev Biol.* 26(2):119-28 (1990). Briefly, 1-mm thoracic aortic rings were placed between two layers of 50 µl growth factor-reduced Matrigel (Becton Dickinson, Bedford, Mass., USA) optionally containing an antibody to be tested, and overlaid with 100 µl of DMEM supplemented with 20 U/ml heparin (Sigma-Aldrich corporation, Saint-Louis, Mo., USA) and ECGS (Upstate biotechnology, Lake Placid, N.Y., USA). Microvessel outgrowth was visualized by phase microscopy using a Zeiss Axioskop microscope.

Tumor Graft

Female 8- to 10-week-old C56BL6/J mice (Charles River laboratories, L'Arbresle, France) were inoculated subcutaneously with $1\times 10^6$ murine Lewis lung carcinoma cells (LLC1). Mice were then injected intraperitoneally every second day with 150 µg of monoclonal antibody H33, isotype matched control antibody Mel14 or PBS. When the control tumors (PBS injected mice) had reached 1-1.5 $cm^3$ animals were sacrificed and tumors were excised and analysed.

Vessels Quantification

Tumor cryosections were stained with monoclonal anti-PECAM-1 antibody as described in Immunostaining Chapter. Pictures of the entire cryosections (4 cryosections per tumor) were taken using a Zeiss Axioskop microscope. PECAM-1 staining and the total area of the tumor were quantified using Zeiss KS400 software.

Evans Blue Permeability Assay

150 µg of anti-JAM-C or isotype-matched control antibodies were injected into the retro-orbital vein of anaesthetised mice. After 15 minutes, 100 µl of a 30 mg/kg Evans blue dye (Sigma-Aldrich corporation, Saint-Louis, Mo., USA) solution in saline was injected in the same way as antibodies, and circulated for one hour. Mice were then perfused with citrate-buffered 1% paraformaldehyde, pH 4.2, 37° C. to clear the dye out of the vessel lumina. Immediately after perfusion, the organs (kidney, lung, heart and brain) were dissected. After drying (Speed-Vac) of the tissue, the dried weight was measured. Evans blue was extracted by subsequent incubation of the tissue in 500 µl of formamide for 18 hours at 70° C. The extract was centrifuged and the absorbance of the supernatant was measured at 620 nm with a spectrophotometer. The dye concentration in the extracts was calculated from a standard curve of Evans blue in formamide and normalized to the dry tissue weight.

Statistical Analysis

Vessel density counts, tumor volume and tumor weight were analysed using the Mann-Whitney's t test. Analyses were computed using the statistical software StatView (Abacus Concepts Inc, Berkeley, Calif., USA).

Results

JAM-C is Expressed by Tumor Vessels and is Receptive to Angiogenic Stimuli

In angiogenic tumor of human liver, anti-JAM-C antibody H36 stains blood vessels (FIG. 1). In contrast, the transcript encoding JAM-C is not present in normal liver. Treatment of HUVECs with VEGF leads to immediate and massive accumulation of JAM-C in endothelial cell-cell contacts within 15 minutes (FIG. 2A). This short appearance is the result of JAM-C relocalization and the expression level is not modified by this treatment (FIG. 2B). The same results were observed when HUVECs were stimulated with TNF-α or thrombin.

In Vitro Vessel Outgrowth is Inhibited by Anti-JAM-C Monoclonal Antibody

In vitro neovascularization was carried out using ex vivo aortic rings assays. Freshly dissected mouse aortae were cut into small rings and those embedded in Matrigel in the presence or absence of anti-JAM-C antibodies. Outgrowth of endothelial vessels from the aortic rings were assessed over a period of 12 days. Whereas the presence of control anti-JAM-C or isotype matched antibodies do not affect aortic sprouting, the H33 anti-JAM-C antibody totally blocks neovascularization (FIG. 3).

Anti JAM-C Monoclonal Antibody Reduces Tumor Growth and Angiogenesis In Vivo

Given that in vitro angiogenesis can be blocked with H33 anti-JAM-C antibody, we investigated whether this antibody had an effect on tumor angiogenesis and tumor growth. Mice were sub-cutaneously injected with Lewis lung carcinoma cells. Anti-JAM-C and control antibodies were then injected intra-peritoneally every second day. Animals were sacrificed when the control tumors reached 1-1.5 cm$^3$ and tumors excised. Tumor size (FIG. 4A), volume (FIG. 4B) and weight (FIG. 4C) were significantly decreased when mice were treated with H33 anti-JAM-C antibody compared with the control isotype matched antibody or PBS.

Representative examples of excised tumors are shown in FIG. 4A. Lewis lung carcinoma cells do not express JAM-C (data not shown). The H33 antibody effect on tumor growth is due to inhibition of angiogenesis. In order to visualize the tumor vasculature, cryosections were immunostained with antibody against the endothelial marker PECAM-1 (FIG. 4D). Blood vessel density was quantified by counting the % of PECAM-1 staining across the area of the tumor (FIG. 4E). The H33 antibody reduced the number of blood vessels in tumors when compared to the controls.

H33 Anti-JAM-C Monoclonal Antibody is Not Toxic In Vivo

It is known that antibodies can be toxic when injected in vivo. In order to control that the observed effect of H33 anti-JAM-C antibody is not due to a general toxic effect in mice it was investigated whether antibody injected animals develop pathologies. Since JAM-C is expressed by endothelium in the kidney it was first analysed whether the antibody would create glomerulonephritis. To this end kidney sections of treated animals were stained with periodic acid-Schiff. No abnormal accumulation of protein in glomeruli was detected (FIG. 5A).

Since JAM-C is involved in controlling vascular permeability it was also tested whether the antibody would induce leakiness of blood vessels. Fortunately this was not the case in heart, lung, kidney or brain, the representative organs analysed (FIG. 5B).

Reduction in the number of glomeruli was observed in the retinas of H33 treated compared to control mice (ctrl) or mice treated with isotype matched control antibody. This indicates a decreased neo-vascularization of retinas in H33 treated animals FIG. 6).

Example 6

Anti-JAM-C Antibody H33 Reduces the Number of Macrophages in Tumors but Affects Neither Proliferation, nor Apoptosis of Endothelial Cells Materials and Methods Histology and Quantification of Vessel Density, Apoptotic Cells and Macrophage Contents into the Tumours For immunohistochemistry on tumor cryosections with monoclonal antibody anti-PECAM-1 (GC51), sections were fixed with acetone/methanol 1:1 for 5 minutes at −20° C., dried and hydrated in PBS/Gelatin 0.2%/Tween 20 0.05%. Sections were incubated with antibody for 1 hour at room temperature and, after 3 washes in PBS, incubated with a secondary antibody coupled to peroxidase (Jackson Immunoresearch Laboratories, Inc., West Grove, Pa., USA).

For immunohistochemistry on paraformaldehyde-fixed and paraffin embedded eye sections with polyclonal antibodies against PECAM-1 and JAM-C, sections were dewaxed following the classical procedure. Tissue sections were then treated with $H_2O_2$ 0.3% in methanol for 10 minutes, washed in PBS and blocked with PBS/BSA 3%/Tween20 0.1% for 30 minutes. Sections were incubated with polyclonal antibodies for 1 hour at room temperature and, after washes in PBS, incubated with EnVision™ system for 30 minutes (DakoCytomation AG, Zg, Switzerland).

Acid phosphatase activity was detected on tumor cryosections using the method previously described in (Kindler, V. et al., Cell, 56: 731-740, 1989). Detection of apoptotic cells on tumor cryosections was based on labelling of DNA strand breaks (TUNELfluorescence method) and were performed using Terminal Transferase and biotin-16-dUTP, according to the manufacturer's instructions (Roche diagnostics AG, Rotkreuz, Switzerland).

Bound biotin-16-dUTP was detected with streptavidin coupled to Texas Red dye (Jackson Immunoresearch Laboratories, Inc., West Grove, Pa., USA).

Pictures were acquired using a Zeiss LSM510 confocal microscope or a Zeiss Axiophot 1 microscope equipped with an Axiocam color CCD camera. Images were recorded and treated using the AxioVision™ software (Zeiss, Oberkochen, Germany).

To quantify the number of acid phosphatase-positive cells (macrophages) and the number of TUNELpositive cells (apoptotic cells) into the tumors, pictures of the entire cryosection (4 cryosections per tumor) were analyzed using Zeiss KS400 or Openlab softwares (Zeiss, Oberkochen, Germany).

MTT Assay for the Determination of Cell Proliferation

The proliferation index of murine primary endothelial cells (LMEC) and tumor cells (LLC1) were determined using MTT (3,(4,5-dimethylthiazol-2-yl)2,5-diphenyl-tetrazolium bromide) method as described in Hansen, M B et al., J Immunol Methods, 119: 203-210, 1989. Briefly, cells were plated in triplicate into 96 well plates at densities ranging from 1.25× $10^4$ to 1×$10^5$ cells per well and cultured in complete medium in presence or absence of 50 mg/ml of anti-JAM-C antibody H33 or control antibody 9B5. After 24 hours of culture, 25 ml of solution of MTT (5 mg/ml in sterile PBS) were added to each well, and after 2 hours of incubation at 37° C., 100 ml of the extraction buffer were added (20% w/v of SDS dissolved in a solution of each DMF and demineralised water; pH was adjusted to 4.7 by adding 2.5% of an 80% acetic acid and 2.5% 1N HCl). After overnight incubation at 37° C. optical densities at 570 nm were measured using a microplate reader (Molecular devices corporation, CA, USA).

Results

H33 anti-JAM-C Antibody Reduces the Recruitment of Macrophages into the Tumors

Tumor angiogenesis is often accompanied by inflammation and macrophages represent prominent tumor-associated inflammatory cells (Crowther, M et al., J Leukoc Biol 70: 478-490, 2001). Indeed, macrophages participate in angiogenesis by secreting angiogenic factors such as VEGF, mostly under hypoxic conditions (Murdoch, C et al., Blood 104(8): 2224-34, 2004). JAM-C is implicated in leukocyte adhesion and transmigration through endothelial and epithelial cells (Zen, K et al., Mol Biol Cell 15: 3926-3937, 2004; Chavakis, T et al., J Biol Chem, 2004; Johnson-Leger, C A et al., Blood 100: 2479-2486, 2002, Cunningham, S A et al., J Biol Chem 275: 34750-34756, 2000).

It was thus investigated whether the H33 antibody might affect recruitment of macrophages into tumors. As shown in FIGS. 7B and 7D, mice treated with H33 antibody showed reduced macrophage content in tumors compared to control mice. This indicates that the H33 effect on angiogenesis is mediated in part via its action on recruitment of macrophages.

The H33 Anti-JAM-C Antibody has no Effect on Endothelial Cell Proliferation or Apoptosis Angiogenesis is a complex process orchestrated by the proliferation and architectural reorganization of endothelial cells upon angiogenic stimuli. It was first tested whether the H33 antibody blocks angiogenesis by inhibiting proliferation of endothelial cells in vitro and found no effect (FIG. 8A). To avoid any direct consequence of H33 treatment on tumor cell proliferation, the experiment was also performed with tumor cells in vitro and no effect was detectable (FIG. 8B).

These results indicated that the reduction of angiogenesis observed after H33 administration is not caused by prevention of vascular or tumor cell growth. Stimulation of apoptosis would be another explanation for the reduction of angiogenesis induced by H33 treatment. This hypothesis was tested on tumor sections by identifying apoptosis by a standard labelling protocol of apoptotic cells (TUNEL). Results revealed that H33 antibody had no consequence on endothelial cell apoptosis in vivo and in vitro (FIG. 8C and data not shown). However, tumor cells showed increased TUNEL labeling in vivo, suggesting that apoptosis occurred as a consequence of antibody-mediated reduced vascularization (FIGS. 8C and D).

The invention claimed is:

1. A labeled angiogenesis inhibiting molecule comprising a label and an angiogenesis inhibiting molecule selected from:
    (a) the antibody H33, produced by hybridoma 13H33 as deposited with the Deutsche Sammlung von Mikroorganismen und Zellkulturen GmbH under the deposit accession number DSM ACC2622, or antigen binding fragments thereof;
    (b) a humanized antibody comprising all of the complementarity determining regions (CDRs) of the H33 antibody;
    (c) a chimeric antibody comprising all of the CDRs of the H33 antibody;
    (d) a fragment of H33 selected from:
        (i) a Fab fragment;
        (ii) a Fv fragment; or
        (iii) a scFv, a dimer of a scFv, a trimer of a scFv or a larger aggregate of a scFv; or
    (e) a recombinant antibody comprising all of the CDRs of the H33 antibody.

2. The labeled angiogenesis inhibiting molecule according to claim 1, wherein said labeled angiogenesis inhibiting molecule further comprises one or two non-immunoglobulin moieties selected from cytokines, interleukins, hematopoietic factors, lymphokines, interferons, or chemokines.

3. The labeled angiogenesis inhibiting molecule according to claim 1, wherein said labeled angiogenesis inhibiting molecule:
    a) blocks angiogenesis in vitro and in vivo;
    b) reduces tumor growth in vivo;
    c) reduces the recruitment of macrophages into tumors; and
    d) blocks the interaction of JAM-C with JAM-B.

4. The labeled angiogenesis inhibiting molecule according to claim 1, wherein said angiogenesis inhibiting molecule is the antibody H33, produced by hybridoma 13H33 as deposited with the Deutsche Sammlung von Mikroorganismen and Zellkulturen GmbH under the deposit accession number DSM ACC2622, or antigen binding fragments thereof.

5. The labeled angiogenesis inhibiting molecule according to claim 1, wherein said angiogenesis inhibiting molecule is a humanized antibody comprising all of the CDRs of the H33 antibody.

6. The labeled angiogenesis inhibiting molecule according to claim 1, wherein said angiogenesis inhibiting molecule is a chimeric antibody comprising all of the CDRs of the H33 antibody.

7. The labeled angiogenesis inhibiting molecule according to claim 1, wherein said angiogenesis inhibiting molecule is a Fab fragment of H33.

8. The labeled angiogenesis inhibiting molecule according to claim 1, wherein said angiogenesis inhibiting molecule is a Fv fragment of H33.

9. The labeled angiogenesis inhibiting molecule according to claim 1, wherein said angiogenesis inhibiting molecule is a scFv, a dimer of a scFv, a trimer of a scFv or a larger aggregate of a scFv of H33.

10. The labeled angiogenesis inhibiting molecule according to claim 1, wherein said angiogenesis inhibiting molecule is a recombinant antibody comprising all of the CDRs of the H33 antibody.

11. A method of binding a labeled angiogenesis inhibiting molecule to JAM-C comprising contacting a sample, under conditions that allow for the binding of said labeled angiogenesis inhibiting molecule to JAM-C, with a composition comprising:
    (a) a labeled angiogenesis inhibiting molecule comprising a label and:
        (i) the antibody H33, produced by hybridoma 13H33 as deposited with the Deutsche Sammlung von Mikroorganismen and Zellkulturen GmbH under the deposit accession number DSM ACC2622, or antigen binding fragments thereof that have the binding specificity of the H33 antibody;
        (ii) a humanized antibody comprising all of the CDRs of the H33 antibody;
        (iii) a chimeric antibody comprising all of the CDRs of the H33 antibody;
        (iv) a fragment of H33 selected from:
            (A) a Fab fragment;
            (B) a Fv fragment; or
            (C) a scFv, a dimer of a scFv, a trimer of a scFv or a larger aggregate of a scFv; or
        (v) a recombinant antibody comprising all of the CDRs of the H33 antibody
        and
    (b) a suitable excipient, carrier or diluent.

12. The method according to claim 11, wherein said method further comprises the detection of the binding of JAM-C to said labeled angiogenesis inhibiting molecule.

13. The method according to claim 12, wherein said sample is a tissue sample, a body fluid sample or a cell sample.

14. The method according to claim 12, wherein said method is ex vivo or in vitro.

* * * * *